Figure 1:
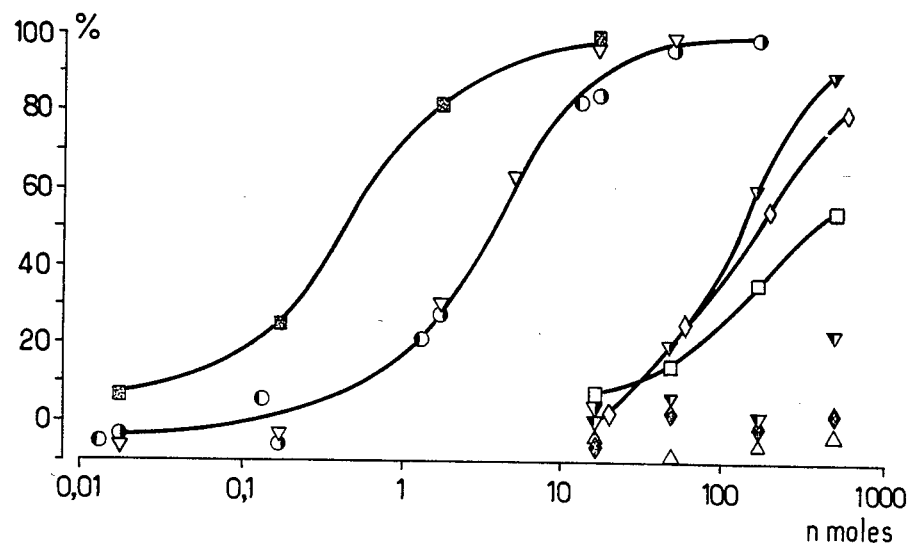

United States Patent [19]

Feizi et al.

[11] Patent Number: 4,563,445
[45] Date of Patent: Jan. 7, 1986

[54] 3-FUCOSYL-N-ACETYL LACTOSAMINE DERIVATIVES, AND THEIR BIOLOGICAL APPLICATIONS

[75] Inventors: Ten Feizi; Hock C. Gooi, both of London, England; Pierre G. Sinay, Orleans, France

[73] Assignee: Choay S.A., Paris, France

[21] Appl. No.: 569,487

[22] Filed: Jan. 9, 1984

Related U.S. Application Data

[63] Continuation of Ser. No. 396,193, Jul. 8, 1982, abandoned.

[30] Foreign Application Priority Data

Jul. 8, 1981 [FR] France ............................ 81 13447

[51] Int. Cl.[4] .............................................. A61K 31/73
[52] U.S. Cl. ........................................ 514/25; 536/4.1; 536/17.2; 536/17.9
[58] Field of Search .................... 536/4.1, 17.2, 17.9; 424/180; 514/25

[56] References Cited

U.S. PATENT DOCUMENTS 4,137,401  1/1979  Lemieux et al. ..................... 536/4.1

*Primary Examiner*—Johnnie R. Brown
*Assistant Examiner*—Elli Peseler
*Attorney, Agent, or Firm*—Omri M. Behr

[57] ABSTRACT

The invention relates to substitution derivatives of trisaccharide 3-fucosyl-N-acetyl lactosamine and to the immunological applications of these derivatives and of the trisaccharide itself particularly as diagnostic reagent and in therapy.

20 Claims, 3 Drawing Figures

3-FUCOSYL-N-ACETYL LACTOSAMINE DERIVATIVES, AND THEIR BIOLOGICAL APPLICATIONS

This application is a continuation of application Ser. No. 396,193, filed 7/8/82, now abandoned 5/15/84.

The invention relates to derivatives of 3-fucosyl N-acetyl lactosamine, their preparation and their biological applications.

It relates more particularly to derivatives of 3-fucosyl-N-acetyl lactosamine having the following trisaccharide sequence

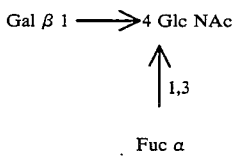

in which Gal represents a galactopyranosyl unit, Glc NAc, a 2-acetamido, 2-deoxy-glucopyranosyl unit (which will be called below glucosamine) and Fuc a fucopyranosyl unit. The 3-fucosyl-N-acetyl lactosamine sequence has already been detected chemically on certain glycoproteins and on certain glycolipids of normal or tumorous tissues. No information has been given however on its distribution in the tissues.

It has been suggested that this structure, present on erythrocytes, can lead, in a particular case to an immunological response. However, no information resulted therefrom on possible detection of this oligosaccharide sequence, as an antigen, in various tissues.

No correlation had therefore been established between the presence of this structure in the tissues and the possibility of detecting it as an antigen.

Moreover, this knowledge could not lead to establishing correlations between the presence of this structure in the tissues and the presence of antibodies against this structure during the normal development of the tissues or in pathological conditions.

In addition, in prior research carried out in this field, the material studies was constituted by natural extraction products. Now, such products often contain contaminants, with undetermined substances, which introduces uncertainty factors as to the specificity of the immunological observations.

It has now been discovered that the 3-fucosyl-N-acetyl lactosamine sequence concerned can only be detected as an antigen under certain conditions. These researches therefore establish that if this structure can be detectable chemically, it does not express itself in all cases as an antigen.

The research which has lead to the development of the invention relates to a study of an antibody, called anti-SSEA 1, formed against a mouse carcinoma. The interest in this antibody resulted from its recognition of an embryionic antigen (of unknown structure) appearing at a stage of the embryonic development of the mouse corresponding to eight cells, or SSEA-1 antigen.

It was then unexpectedly found that anti-SSEA 1 recognised structures containing the 3-fucosyl-N-acetyl lactosamine sequence concerned. Demonstration of the specific recognition of this structure by the antt-SSEA 1 antibody has been made by using the trisaccharide obtained synthetically and thereby of high purity and specificity.

It has thus been possible to establish that the antigenicity of SSEA-1 resulted from the 3-fucosyl-N-acetyl lactosamine sequence.

Study of the conditions and of the tissues in which the sequence concerned is not only present, but where its antigenicity can be expressed has permitted another step of the invention to be realised by leading to the study of the utility of 3-fucosyl-N-acetyl lactosamine and of substitution derivatives of this trisaccharide, as well as of antibodies formed by the trisaccharide and its substitution products, in particular under a conjugated form for diagnosis and in therapeutics.

It is therefore an object of the invention to provide novel derivatives of trisaccharide 3-fucosyl-N-acetyl lactosamine, useful as biological reagents or facilitating by their nature the exploitation of the properties of the trisaccharide concerned. Its purpose is also to provide access routes to these trisaccharides.

It is also an object to provide uses, as an antigen determinant, of 3-fucosyl-N-acetyl lactosamine trisaccharide and of its derivatives, in particular, the antigen reagents and the antibodies developed from these products as well as the immunoabsorbants resulting from the coupling of these products to solid supports.

The novel trisaccharides of the invention are substitution derivatives of the trisaccharide O-α-L-fucopyranosyl-(1→3)-[O-β-D-galactopyranosyl-(1→4)-2-acetamido-2-deoxy-D-glucopyranose] (this trisaccharide is denoted in the specification and the claims by the term 3-fucosyl-N-acetyl lactosamine) and corresponds to the formula:

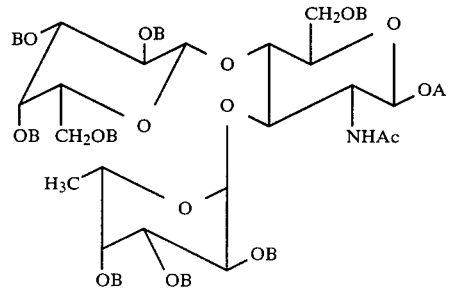

in which:

A represents:

an alkyl group comprising 2 to 10 carbon atoms, or a hydroxy-alkyl group with 2 to 10 carbon atoms including one or several hydroxyl groups, advantageously a hydroxyl group at the end of the chain, or a group including one or several unsaturated bonds, in particular at least an ethylenically unsaturated radical, selected from alkenyl radicals, and more especially alkenyl radicals with 2 to 10 carbon atoms, or again one of the preceding groups, but including one or several intercalary ether and/or amine groups, the various groups represented by A end in a nitrogen group particularly amino, amido, hydrazino, azido, or a carboxylic acid group or a derivative thereof, particularly an ether or an ester, the substituants B, identical or different from one another, represent, as the case may be with a neighbouring substituent, hydroxyl radical protective groups and are selected from among stable groups, unreactive under the usual oside synthesis conditions and easily removable under gentle conditions, compatible with the maintenance of the oside structure, in particular, by benzyl, benzylidenyl, benzoyl, or acetyl groups, or represent a hydrogen atom.

In a preferred group of oside derivatives according to the invention, A represents an alkyl radical comprising 2 to 10 carbon atoms, substituted by at least one hydroxyl group, advantageously at the end of the chain, particularly an alkyleneglycol or hydroxyalkyl radical, or a carboxylic group or a derivative thereof.

Products of that kind, in particular those, in which A represents and $\alpha$, $\beta$-dihydroxypropyl, $\beta$-hydroxyethyl or $\gamma$-hydroxypropyl group, constitute especially interesting biological reagents in biological applications using their binding on a protein or an insoluble support having free amino functions, for example, for the constitution respectively of artificial antigens and of immunoabsorbants.

In another preferred groups of trisaccharides of the invention, A is terminated by a nitrogenous group, particularly by an amino, amido, azido or hydrazino group.

Another preferred group of trisaccharides includes, optionally further to at least one of the above features, one or several intercalary ether groups, particularly two or even three ether functions.

Still another preferred group comprises chains A with an alkaline group terminated by a functional group.

Preferred trisaccharides of the above groups contain a chain A having the following structure (1), (2) or (3):

(1):—$(CH_2)_n$—O—$(CH_2)_{n'}$—O—$(CH_2)_m$—R (2):—$(CH_2)_{n''}$—O—$(CH_2)_{m'}$—R (3):—$(CH_2)_{n'''}$—R wherein:
n, n' and m, identical or different each from other are equal to 1,2,3,4 or 5, m being further optionally equal to 0, the sum n+n' and optionally m being advantageously a number from 4 to 10, preferably equal to 6;
n'' and m', identical or different each from other, being equal to 1,2,3,4 or 5, m' being further optionally equal to 0, n'' or optionally n''+m' (if m' is different from 0) being advantageously a number from 4 to 10, preferably equal to 6 or 8,
n''' is a number from 1 to 10, advantageously from 4 to 10, preferably equal to 8, and
R is a functional group.

Preferred products have chains A wherein R represents a nitrogenous group such as
$NH_{2'}$—$N_3$ or $NH$—$NH_2$.

In other chains of structures (1) or (2), R represents an hydrogen atom.

Other preferred chains of structures (1), (2) or (3) above contain a group R being a —COOR' or —COR' group, R' representing an hydrogen atom or an alkyl radical with 1,2 or 3 carbon atoms or again R represents a —CONH$_2$ group.

Other preferred trisaccharides include a chain A such as above defined with one or several intercalary amine groups.

Trisaccharides also advantageous, particularly as intermediate compounds for obtaining the desired trisaccharides correspond to products in which A has the structure (1), (2) or (3) as above, in which R represents an alkenyl group with 2 to 10 carbon atoms, preferably an allyl group.

The preparation of these novel trisaccharides is advantageously integrated into the process of synthesizing three 3-fucosyl-N-acetyl lactosamine trisaccharide described by JACQUINET and SINAY in J.Chem.Soc. p 314–318, 1979.

It is recalled that, in its most general reaction scheme, this process comprises, in a first step, the reaction of 2,3,4,6-tetra-O-acetyl-$\beta$-D-galactopyranosyl bromide with benzyl-2-acetamido-3-O-allyl-6-O-benzyl-2-deoxy-$\alpha$-D-glucopyranoside in 1,2-dichloroethane, in the presence of mercuric bromide and a 4 Å molecular sieve. The resulting product is then constituted by benzyl 2-acetamido-4-O (2,3,4,6-tetra-O-acetyl-$\beta$-D-galactopyranosyl)-3-O-allyl-6-O-benzyl-2-deoxy-$\alpha$-D-glucopyranoside. In a second step, the ally group is removed with chloro (tristriphenylphosphine)-rhodium and the product obtained is condensed with 2,3,4-tri-O-benzyl-$\alpha$-L-fucopyranosyl bromide. The acetyl groups are then removed and the 3-fucosyl lactosamine trisaccharide is obtained after catalytic hydrogenolysis.

Within the scope of the invention, this scheme is hence advantageously used; however it is effected by applying a glucopyranose, modified so as to include the desired substituent branch.

According to a preferred embodiment of the invention, diethylene glycol or triethylene glycol are used for making products having chains of the type (1), i.e. including at least two intercalary ether groups.

This embodiment has the advantage of enabling the use of an inexpensive product and whose reactivity offers access to numerous substitutions.

The developed chains are then condensed with a reactive derivative of glucosamine mentioned in accordance with the above mentioned method of synthesis of JACQUINET and SINAY, for example, the chloride of this glucosamine or a glucosamine having all the positions blocked except the fourth one. The resulting disaccharide is applied in the process concerned wherein it is condensed with a reactive fucosyl derivative.

In another modification, which permits more especially the production of trisaccharides substituted on the glucosamine unit by a chain of structure (3) recourse is advantageously had to conventional methods of the KOENIGS-KNORR type comprising the reaction of a reactive derivative of a $\beta$-glucosamine, such as 1,2-oxaline, with a monocarboxylic acid of the structure:

HO—$(CH_2)_{n'''}$—R in which n''' and R have the meanings given above with respect to structure (3).

The $\beta$-glucosamine of the formula:

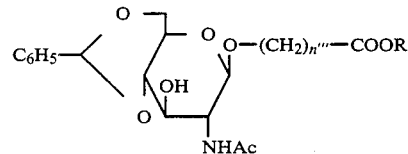

is then integrated into the process of JACQUINET and SINAY.

According to another embodiment enabling the trisaccharides of the invention to be obtained in which A represents an allyl group or a chain which can be obtained by using the reactivity of the allyl group, the synthesis of a trisaccharide corresponding to the structure of the trisaccharides of the invention is first done. In this trisaccharide all the —OH groups located inside protective groups, and are advantageously benzylated. In accordance with conventional reactions of organic synthesis, an allyl-group is introduced into the 1 position, at β, of the glucosamine.

From allyl-1-β-glucosamine, due to the reactivity of the allyl group, it is possible to proceed with the extension of the chain so as to introduce the various groups desired. The articulation of the various reactions involved is effected according to conventional synthetic techniques.

It is particularly advantageous, to extend the allyl chain, to subject the allyl derivative to a hydroboration reaction, using a reagent such as 9-borabicyclo/3.3.1-/nonane, then to the action of a base.

A corresponding chain terminated by a functional alcohol group is then obtained. It will be noted that this group can easily be etherified and permits the introduction of an intercalary ether group into the substitution chain A, the other hydroxyls of the trisaccharide being protected by benzyl ethers.

When it appears desirable, for specific applications to have a chain serving as a coupling arm to be fixed to a support, the preceding chain with an alcohol group is treated with an allyl halide to introduce a new allyl group which will in turn advantageously be subjected to a hydroboration reaction.

This set of reactions enables the increase, as desired, of the length of the substituent chain and to have at the end of the chain functional groups enabling through their reactivity better exploitation of the properties of the osides of the invention.

Among the various possibilities of treatment offered, it is advantageous to choose tosylation and then to react the tosylated derivative with an azide.

As indicated above, the researches which are the basis of the development of the invention have shown that the 3-fucosyl-N-acetyl lactosamine sequence was detectable as an antigen and that it was only expressed under certain conditions and in certain tissues where the density of this sequence was relatively high. A series of radioimmunological test results carried out in this respect are given below by way of illustration.

The invention then provides means enabling the detection of this sequence to be ensured, and of exploiting this detection in various immunological applications of great interest.

The invention concerns, in particular, diagnostic reagents, exploiting the antigen character of the 3-fucosyl-N-acetyl lactosamine trisaccharide, or of its abovedefined substitution derivatives. These reagents are useful as such or in immobilized form. The invention also concerns the antibodies raised against this trisaccharide and its derivatives.

These antigen reagents are reference compounds and show themselves to be especially valuable for the characterisation of structures and antibodies. In particular, they can be used to detect the presence of antibodies or to study the variations in the antibody levels under various conditions associated with cellular development (embryogenesis) or with pathological conditions which then correspond to a stage in which the antigenic character of the 3-fucosyl-N-acetyl lactosamine sequence was expressible.

They have, in particular, great interest in the detection of antibodies released in the course of auto-immune disorders, and disorders of pregnancy (notably in the case of toxemias, eclampsias, and patients afflicted with certain cancers or again in the case of teratocarcinomas.

The invention is also intended for research on specific antibodies formed against the 3-fucosyl-N-acetyl lactosamine trisaccharide and its substitution derivatives of high purity according to the invention.

Advantageously, these specific antibodies enable determination of how the antigenicity of the trisaccharide structure concerned can be affected during the cellular development and, generally, if this structure is expressed as an antigen in the tissues.

Such products, which are advantageously labelled, either by radioisotopes or by fluorescent substances or other biochemically detectable substances to facilitate localizations, constitute valuable reference compounds by enabling recognition of the 3-fucosyl-N-acetyl lactosamine structure as an antigen in complex sequences of biological material.

In that respect, the advantage of easily obtaining production of high purity, due to their possible production by the synthetic route, can be appreciated.

These antigenic reagents of high purity can thus be advantageously used for detecting and/or studying polyclonal or monoclonal antibodies.

As shown by the works disclosed by H. KOPROWSKI at the Federation Meetings at New Orleans in April 1982, to which it is referred in Fed. Proceeding Abstracts, 3rd volume, V. GUINZBURG and H. KOPROWSKI, the 3-fucosyl-N-acetyl lactosamine is present in gastroinstestinal tumors. The advantage of being able to detect such a kind of tumors with the pure products of the invention will be appreciated.

These works added to those here described of the inventors show the wide scope of application of the products of the invention.

The invention thus provides biological reagents useful in a large scale. Their production by the synthesis route makes their preparation easier under a form appropriate to a specific use. The invention enables to have a wide range of reagents for the various immunological applications of these products.

3-fucosyl-N-acetyl lactosamine and its derivatives according to the invention are also advantageously applied, as reference compounds to develop enzyme substrates, in particular, substrates of glycosidases and glycosyl-transferases.

The above-defined substitution chains enable exploitation of the antigen properties of 3-fucosyl-N-acetyl lactosamine trisaccharide in artificial antigens or in immunoabsorbents. These chains constitute in fact valuable spacer arms enabling, according to their nature, fixation to proteins or various types of insoluble supports for the purpose of developing respectively artificial antigens and immunoabsorbents.

The invention comprises also these artifical antigens and these immunoabsorbents as novel products.

For the development of artificial antigens, trisaccharides are used whose chains end more especially in a —COOH or —NH$_2$ group, coupling being effected on a carrier macromolecule which can be administered to the animal. Chains terminated by a —OH or —COOH group or a derivative thereof are advantageously fixed on macromolecules such as those of the groups comprising poly-L-alanine-lysine, albumin, bovin serum albumin, thyroglobulin and polylysin.

The chains possessing at least one intercalary ether function and advantageously two or three, that is to say within the chain, have a valuable hydrophilic character.

Chains of this type terminated by an amino group are particularly advantageous for coupling the trisaccharide to solid supports of high stability, possessing —OH or —COOH or —CONH$_2$ fixing sites.

The substituent chains of the trisaccharides of the invention thus enable access to supports resulting in specific immunoabsorbent having a high absorption capacity of anti-3-fucosyl lactosamine antibodies and not resulting in non-specific absorptions.

Supports advantageously chosen are those based on polymers including polysaccharides especially cellulose or agarose or cross-linked agarose (particularly those under the trademark Sepharose of Pharmacia).

Other suitable supports include silica, glass or latex beads or mixed polymers also including, other polymer derivatives such as polyacrylamides or polyacrylics.

The supports of this type, within the framework of the invention, are those marketed under the trademarks ULTROGEL or MAGNOGEL by IBF (Industries Biologique Francaise).

In general, in order to prevent any non-specific fixing, the coupling product is advantageously suspended in a solution enabling the saturation of fixing sites which are still free.

This suspention can be, for example, carried out in a protein solution.

In order to couple the invention's products to the supports of the above mentioned type, it is advantageous to use general methods employed in affinity chromatography.

According to current techniques, the solid support on which it is desired to immobilize the oside derivative is previously activated. This activation can be carried out by different means, for example, by means of cyanogen bromide, carbonyldiimidazole, hydrazine or glutaraldehyde or any other known equivalent product to this purpose.

The invention hence provides particularly valuable synthetic immunoabsorbents, enabling the development of test-serums with 3-fucosyl-lactosamine specificity or devoid of anti-3-fucosyl-lactosamine antibodies which it is desired to eliminate.

The particular advantage of the immunoabsorbents of the invention is that they can be regenerated. Thus, after elution in an acid medium of the anti-3-fucosyl-N-acetyl lactosamine fixed to immunoabsorbents and concentration, the anti-3-fucosyl-N-acetyl-lactosamine antibodies are eliminated and immunoabsorbents can be used again. The anti-3-fucosyl-N-acetyl lactosamine's are thus recovered with high titers.

Other features and advantages of the invention will emerge from the examples which follow with reference to the Figures.

EXAMPLE 1

Preparation of the trisaccharide 8-azido-3,6-dioxa octyl 2-acetamido-3-O-[α-L-fucopyranosyl]-4-O[β-D-galactopyransoyl]-2-deoxy-β-D-glucopyranoside (compound a)

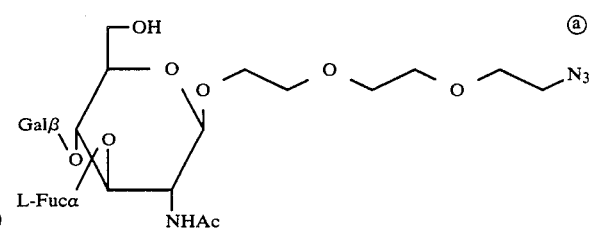

in which Gal and Fuc have the above meanings and Ac is an acetyl group.

Procedure is then according to the method of JACQUINET and SINAY described in J. Chem. Soc. p.314–318, 1979, but in place of benzyl glycoside (a), a β-glycoside is used with

HO—(CH$_2$)$_2$—O—(CH$_2$)$_2$—O—(CH$_2$)$_2$N$_3$

This azide is obtained by means of three steps:
(a) monotosylation of triethyleneglycol
(b) formation of the corresponding azide derivative
(c) condensation with 2-acetamido-3,4,6-tri-O-acetyl-2-deoxy-α-D-glucopyranosyl chloride.

Each of these steps is carried out by proceeding as follows:
(a) monotosylation of triethyleneglycol

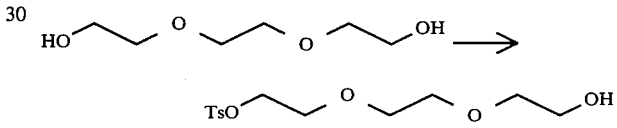

where Ts represents the tosyl group. 1 g of triethyleneglycol is dissolved in 10 ml of anhydrous pyridine; it is cooled to 0° C., then a solution of 1.26 g of tosyl chloride (that is to say one equivalent) in 5 ml of pyridine is poured in drop by drop and the mixture is stirred for 4 hours. Ice water is then added; then the resulting mixture is subjected to stirring for one hour. The conventional treatment (extraction by means of chloroform, washing the chloroform phase with water and drying with sodium sulfate) results in a residue which is purified by chromatography on a silica gel column.

Yield: 60 to 75% of triethyleneglycol monotosylate
(b) conversion to the corresponding azide derivative

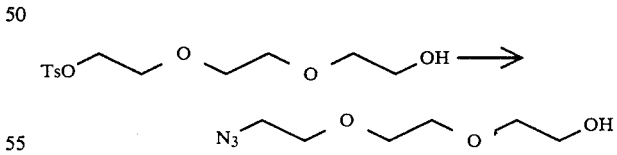

20 g of monotosyl derivative is dissolved in 20 ml of anhydrous DMF, 8.5 NaN$_3$ (2 equivalents with respect to the monotosyl derivative), the mixture is subjected to stirring for 1 hour at 80° C., then cooled. Then the insoluble salts are moved by filtration on sintered glass. After several washed with chloroform, the overall filtrate is recovered (including here the chloroform wash liquors) and it is washed with water to a neutral pH.

The organic phase is dried with sodium sulfate and evaporated under vacuum. The DMF is removed under 10 mm of mercury between 80° and 120° C., then the dried product, is distilled under 10 mm of mercury at about 150° C. In this way there is obtained, in this manipulation about 7,5 g of product, which represents a yield of 65% of azide. An additional distillation under $10^{-3}$ mm of mercury results in the product having a boiling point of 60° C.

Elementary analysis:

|  | Calculated | Found |
|---|---|---|
| Carbon | 41.13 | 41.34 |
| Hydrogen | 4.48 | 7.54 |
| Nitrogen | 23.99 | 23.61 |

(c) condensation with 2-acetamido-3,4,6-tri-O-acetyl-2-deoxy-α-D-glucopyranosyl chloride 12.5 g of acetochloro N-acetylglucosamine, 3 g of the preceding azide derivative, 3 g of 4 Å molecular sieve, 2 ml of tetramethylene, 20 ml of anhydrous dichloromethane, are reacted and the mixture is stirred at 0° C. for 30 min. 7 g of silver triflate are then added, then this mixture is subjected to stirring sheltered from light and moisture for 17 hours at ambient temperature.

After having carried out the usual treatment, (dilution with water, extraction by means of chloroform, washing the chloroform phase with water and drying the chloroform phase with sodium sulfate), the residue obtained is subjected to chromatography on a silica gel column of 250 g using ether-methanol as eluent (20:1 volume of methanol). 6.5 g of crystalline product are obtained.

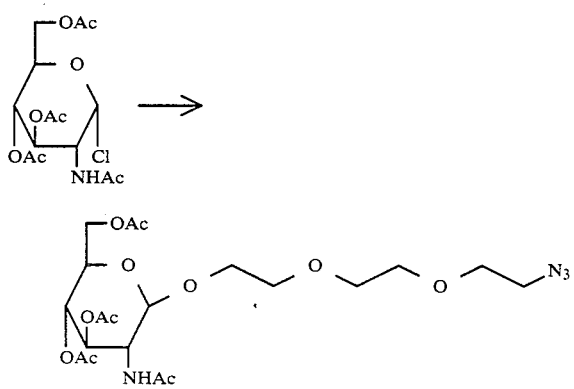

Yield: 75%

An additional 1.3 g of product are obtained by treating the products remaining at the surface of the column, which corresponds to a total yield of 90%.

The physical and analytical characteristics of this product are the following:

| PF | = 69–70° C. |
|---|---|
| $[\alpha]_D^{20° C.}$ | = −29.6° (c = 1.08, chloroform) |

Elementary analysis:

|  | Calculated | Found |
|---|---|---|
| Carbon | 47.61 | 47.48 |
| Hydrogen | 6.39 | 6.17 |
| Nitrogen | 11.10 | 10.89 |

In the course of an additional step, elimination of the acetyl groups follows by operating as follows: 500 mg of the tetraacetylated product are dissolved in 10 ml of anhydrous methanol; some drops of a solution of sodium methoxide in methanol are added and the mixture is subjected to stirring for 2 hours at room temperature. The usual treatment mentioned above is followed by purification on silica gel. 285 mg of product are recovered.

Yield 75%

Elementary analysis of the purified product is as follows:

|  | Calculated | Found |
|---|---|---|
| Carbon | 44.44 | 44.65 |
| Hydrogen | 6.93 | 7.00 |
| Nitrogen | 14.81 | 14.65 |

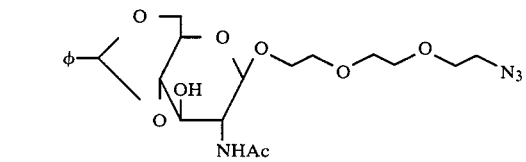

The "deacetylated" product can be used as such, that is to say without prior purification to form the derivative:

wherein φ represents a—$C_6H_5$ group. 300 mg of the deacetylated product are dissolved in 6 ml of anhydrous DMF, 133 mg of dimethoxy toluene are added, a catalytic amount of paratoluene sulfonic acid, and the reactor is left on an evaporator of the Buchi type of which the water-bath is kept at 55°–60° C. for one hour. The reaction mixture is then cooled, is diluted with chloroform and washed with a solution of sodium carbonate and then with a solution of sodium chloride. After drying the organic phase over sodium sulfate and evaporation, a residue is obtained which is recrystallized in ethanol, which results in 304 mg (yield 82%) of a crystalline product having the following characteristics:

| PF | = 193–194° C. | |
|---|---|---|
| $[\alpha]_D^{20° C.}$ | = 76.5° (c = 1.62 chloroform) | |
| Elementary analysis | Calculated | Found |
| Carbon | 54.07 | 54.24 |
| Hydrogen | 6.48 | 6.34 |
| Nitrogen | 12.01 | 12.14 |

EXAMPLE 2

Preparation of the trisaccharide 8-amino 3,6 dioxaoctyl 2 acetamido-3-O-[α-L-fucopyranosyl]-4-O-[β-D-galactopyranosyl]2-deoxy-β-D-glucopyranoside (compound

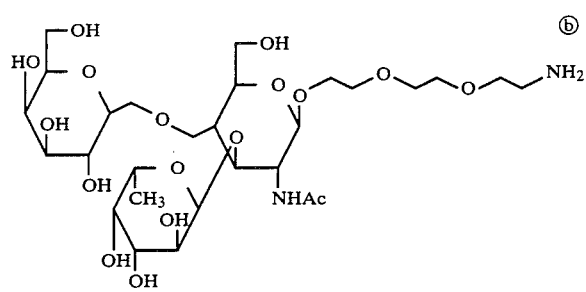

The azide derivative obtained in Example 1 is subjected to the action of sodium methylate, in the presence of methanol, then it is hydrogenated in the presence of Pd/C and CH₃COOH which results in the desired product.

EXAMPLE 3

Preparation of the trisaccharide corresponding to the formula given in Example 2, but in which the substituent chain is constituted by the group —O—(CH₂)₈—COOCH₃, i.e. trisaccharide 8-methoxy carbonyl octyl 3,6 dioxa 2-acetamido 3-O[α-L-fucopyranosyl]4-O-[β-D-galactopyranosyl]2-deoxy β-D glucopyranoside. (compound c). This product is obtained by subjecting the compound of formula d.

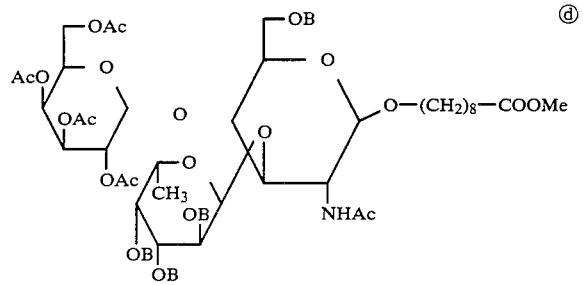

to the treatment given in Example 2.

EXAMPLE 4

Preparation of 7 methoxy carbonyl 3,6 dioxa heptyl 2 acetamido 3-O[αL-fucopyranosyl]4-O[βD-galactopyranosyl]2 deoxy β-D-glucopyranoside (compound 17) of the formula

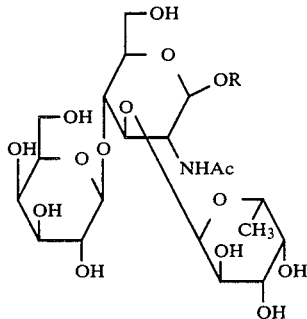

The synthesis is carried out according to the following steps (a) to (p):

(a) preparation of 7-phenyl 3,6 dioxa heptanol (compound 2) according to the following reaction scheme

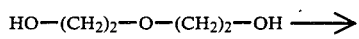

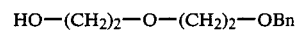

90 g of KOH (powder) and 500 ml of dioxane are mixed in a flask with mechanical stirring. The mixture is heated at 90° C. 90 ml of diethyleneglycol diluted with 100 ml of dioxane and then 108 ml of benzyl chloride are added.

After 30 mn the mixture becomes thick.

100 ml of dioxane are added. The reaction is followed by thin layer chromatography (TLC) with CHCl₃—MeOH=9/0.5. 40 ml of water are added and the stirring is maintained during 30 mn.

The solution is then concentrated, extracted ethyl acetate and washed with water (the monobenzyl compound and traces of the dibenzyl compound are then extracted).

The organic phase is concentrated. The resulting syrup is dissolved in a mixture of hexane-water (the dibenzyle is found with hexane). Chloroform is added to the aqueous phase to extract the monobenzyl compound. The organic phase is dried with sodium sulfate, filtrated, concentrated and distilled under vacuum (5 mm Hg)

E.P.=110°–120° C.

105,6 g are obtained (yield: 63.46%).

(b) Preparation of 9-phenyl-2,5, 8 trioxa 1-methoxycarbonyl nonyl (compound 3) according to the following scheme

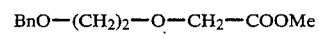

270 ml of anhydrous DMF and 9.66 g of NaH 50% (1/1 equivalent) deoiled with toluene are added to 34.34 g of the monobenzyl compound (0.175 mole).

After 1 h stirring at −10° C., under argon, 40.15 g (22 ml) of methylbromoacetate (1.5 equivalent) are added drop by drop (one hour).

The reaction is finished one hour later (TLC with CH₂Cl₂/aceton: 4/1). 40 ml of methanol and 5 ml of acetic acid are then added. After one hour stirring, the solution is concentrated and extracted with dichloromethane. The organic phase is dried with sodium sulfate, filtrated and concentrated. The resulting liquid is distilled under vacuum E.P. 130°-150° C. (5 mm Hg)—24.7 g of product are obtained (yield: 52.6%).

The NMR spectrum comprises the following signals (CCl₄): δ=3.56-3.62 m 8H (CH₂—CH₂); 3.65 s (3H)OCH₃; 4.03 s (2H) O—CH₂CO; 4.50s(2H) CH₂φ; 7.23 m(5H)φ aromatic (c) Preparation of 7 carboxymethyl 3,6 dioxa heptanol (compound 4) according to the following scheme

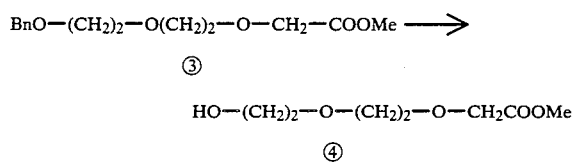

10 g of the starting product are dissolved in 100 ml of anhydrous methanol. The catalyst (Pd/C,10%) is added and the mixture is stirred during one day under hydrogen pressure. The solution is filtrated and then concentrated. The resulting liquid is distilled under vacuum (5 mm Hg) E.P.=120°-130° C.

5 9 g are obtained (yield: 90%).

The NMR spectrum comprises the following signals:

(CCl₄):δ=3.10s(1H)OH;3.56-3.62 m (8H)

CH₂—CH₂; 3.65s(3H)OCH₃; 4.05s(2H)O—CH₂CO.

(d)—Preparation of 7 methoxycarbonyl 3,6 dioxa heptyl-2-acetamido-3,4,6 tri-O-acetyl-2-deoxy-β-D-glucopyranoside (compound 5) according to the following scheme:

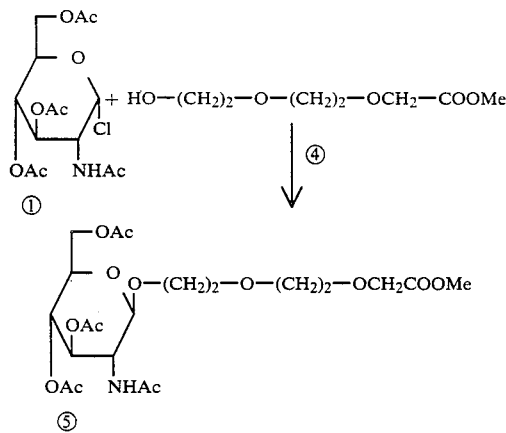

Compound 1 (2-acetamido-3,4,6 tri-O-acetyl 2 deoxy-α-D-glucopyranosyle chloride) is prepared according to the method of D. Morton in Meth. in Carbohydrate Chemistry VI p 282.

1 g of compound 4, 2.5 g of compound 1, 1 g of powdered CaSO₄, dried in a drying oven at 400° C. during 24 h and 10 ml of CH₂Cl₂ (distilled on P₂O₅) are stirred, sheltered from light, and under argon.

The mixture is vigorously stirred during one hour at the ambient.

3 g of HgCN₂ (finely ground) are added and dried during 24 h at 50° C. under vacuum. The mixture is left under stirring during 30 h at the ambient, then diluted with chloroform, filtrated on Celite 545 and washed with sodium bicarbonate, 10% potassium iodide and water.

The organic phase is dried with sodium sulfate, filtrated and concentrated. The resulting syrup is chromatographied (100 g of silicagel; eluent: ether-methanol: 10/0.5).

A colourless syrup is obtained (1 9 g, 67 8%) [α]_D^{20}= −30,6 [c=1.11 CHCl₃]

The NMR spectrum comprises the following signals: (CDCl₃): δ=1.8-2.3 (12H) CH₃CO N—CH₃; 3.5-4.5 m (18H) bras+H₂ H₅ H₆ H₆'; 4.95-5.12 m (3H) H₁ H₃ H₄; 6.90d (1H) NH; J_{NH,H2}=9 Hz.

(e)—Preparation of 7-methoxycarbonyl 3,6 dioxa heptyl, 2 acetamido 2-deoxy-β-D-glucopyranoside (compound 6) of the formula

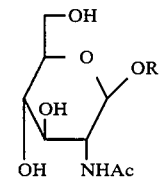

wherein R represents the chain —O(CH₂)₂—O—(CH₂)₂—O—CH₂—COOMe.

1 g of the starting product is dissolved in 10 ml of absolute methanol. Some drops of a sodium methylate 2M solution are added and the mixture is stirred during 2 hours at the ambient. The reaction is followed by TLC (CHCl₃—MeOH 7/3).

After 2 h, a dry H⁺ resin is added (washed with methanol up to neutral pH).

The mixture is filtrated and then concentrated. The resulting syrup is chromatographed (silicagel column=30 g of silicagel; eluent CHCl₃—MeOH 7/3) 650 mg of a white foam are obtained (yield 86.5%)

[α]_D^{20}= −21.6°(c=0.6 MeOH).

(f)—Preparation of 7-methoxycarbonyl 3,6 dioxa heptyl 2 acetamido 4,6-O-benzylidene 2 deoxy β-D-glucopyranoside (compound 7) of the formula

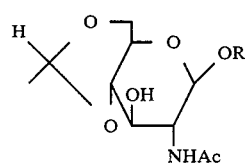

The method of M. E. EVANS in Carb. Res. 21 (1972) 473 is used.

600 mg of the starting material are dissolved in 5 ml of anhydrous DMF.

263 mg of α,α dimethoxy-toluene and a catalytic amount of paratoluene sulfonic acid are added. The reaction is carried out in a rotative evaporator at 55°-60° C. during 1 h. The reaction is followed by TLC (CHCl₃—MeOH: 10/1).

The mixture is extracted by chloroform and the organic phase is washed with water up to neutral pH and concentrated.

After recrystallization in ethanol, 620,4 mg (yield: 84%) M-P: 162° C.; $[\alpha]_D^{20} = -69°(c=1,CHCl_3)$.

The NMR spectrum comprises the following signals: CDCl$_3$ δ: 2.02S(3H) N—CH$_3$; 3.5–3.75 m (11H) CH$_2$—CH$_2$; OCH$_3$; 4.15 s (2H) O—CH$_2$—CO; 4.20–4.50 m (2H); 4.82 d (1H) H$_1$; J$_{1,2}$=8 Hz; 5.54 s (1H)CH-φ; 7.00 d NH; J$_{NH,H2}$=6 Hz; 7.2–7.6 m aromatic.

(g)—Preparation of 7-methoxycarbonyl 3,6-dioxaheptyl 2 acetamido 3-O-benzyl-4,6-O-benzylidene 2-deoxy-β-D-glucopyranoside (compound 8) of the formula

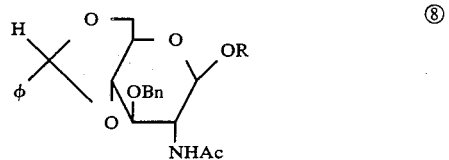

500 mg of the starting material, 980 mg of BaO, 270 mg of Ba (OH$_2$), 8 H$_2$O, 5 ml of anhydrous DMF are vigorously stirred, sheltered from moisture, during 30 mn and then 0.2 ml of benzyl bromide are added.

The mixture is stirred during 3 h. The reaction is followed by TLC (CHCl$_3$—MeOH: 10/1). Hydrolysis of the methyl ester is observed. 5 ml of MeOH are added. After 30 mn stirring, the solution is concentrated and extracted by chloroform.

The organic phase is washed with water, dried with sodium sulfate, filtrated and concentrated. The crystalline residue is dissolved in anhydrous methanol.

A solution of diazomethane in ether is added up to maintainance of a yellow colour. A product migrating more than the starting material is obtained. After 1 h, the reaction mixture is concentrated.

After recrystallisation in methanol, 435 mg of product are obtained (yield: 73%) MP: 182°-184° C.; $[\alpha]_D^{20}= -16.6$ (c=1.02;CHCl$_3$).

The NMR spectrum comprises the following characteristics.

(CDCl$_3$): δ=1.92 s (3H) N—Ac; 3.55–3.90 m (11H) CH$_2$CH$_2$, OCH$_3$; 4.00 s (2H) OCH$_2$CO; 4.20–5.00 m H$_3$,H$_4$,H$_1$CH$_2$φ; 5.56 s (1H) CHφ; 6.80 d NH; J$_{NH,H2}$=8 Hz; 7.20–7.50 m (10H) aromatic.

(h)—Preparation of 7 methoxycarbonyl 3,6 dioxaheptyl 2 acetamido 3-O-benzyl 2-deoxy-β-D-glucopyranoside (compound 9) of the formula

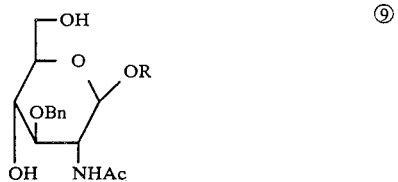

869 mg of starting material and 30 ml of CH$_3$ COOH 75% are heated at 70° C. during 1 h. The reaction is followed by TLC (CHCl$_3$—MeOH=9/1). The solution is extracted and evaporated with toluene.

The resulting syrup is chromatographied silicagel column (25 g), eluent=CHCl$_3$—MeOH (9/1). 660 mg of a coulourless syrup are obtained (yield 90%) (recrystallization in a mixture methanol-ether; the crystals are very hygroscopic; the syrup is used as such).

$[\alpha]_D^{20}= -20.72$ (c=2.3;CHCl$_3$)

The NMR spectrum comprises the following signals: (CDCl$_3$): 1.92 s (3H)N-Ac: 2.82 s (2H)OH; 3.5–3.72 m OCH$_3$—CH$_2$—CH$_2$; 4.08 —O—CH$_2$CO; 4.7–4.8 m 3H H$_1$φ CH$_2$; 6.54 d (1H) NH; J$_{NH,H2}$=8 Hz; 7.3 s (5H)aromatic.

(i)—Preparation of 7 methoxycarbonyl 3,6 dioxaheptyl 2-acetamido 6-O-benzoyl 3-O-benzyl-2-deoxy-β-D-glucopyranoside (compound 10) of the formula

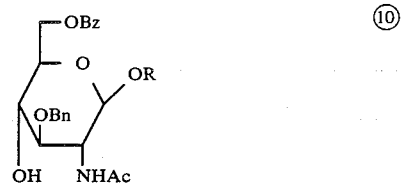

wherein Bz represents a benzoyl group. 660 mg of the starting material are dissolved in 15 ml of dichloromethane (distilled on P$_2$O$_5$). 300 mg of benzoyl cyanide and 3,5 ml of anhydrous pyridine are added.

The reaction mixture, sheltered from moisture, is stirred. The reaction is followed by TLC (CHCl$_3$—MeOH: 9.5/0.5).

At the end of the reaction, anhydrous methanol (5 ml) are added. After 2 h stirring, the solution is concentrated, coevaporated with pyridine and toluene.

White crystal are obtained.

Recrystallization in dichloromethane. Ether (605. 2 mg; yield: 75%). $[\alpha]_D^{20}= -17.5°(c=1,CHCl_3)$; MP=124°-125° C.

NMR spectrum (CDCl$_3$): δ=1.95 (3H) N—Ac: 3.50–3.80 m (14H) amongst them O—CH$_2$—CH$_2$—O, OCH$_3$; 4.09 (2H) OCH$_2$CO; 4.60 s (2H); 4.75 (3H); 6.50 d (1H) NH; 7.20–7.60 (8H) benzyl,benzoate,meta, para; 8.10 d (2H) benzoate (ortho).

(j)—Preparation of 1-O-trichloroacetimidyl 2,3,4,6-tetra-O-acetyl-α-D-galactopyranoside (compound 11) of the formula

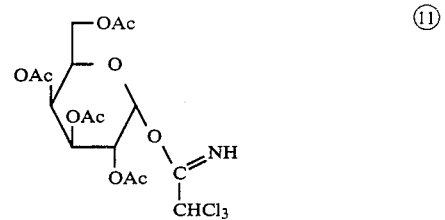

2.4 g of tetra-O-acetyl galactose, prepared according to R. R. SCHMIDT and J. MICHEL Ang. Chem. Int ed (19) (1980) 731–32, F. CRAMER. H. PAWELZIK, H. J. BALDAUF. Ber. (1958) 1049–54, are dissolved in 20 ml of anhydrous dichloromethane.

250 mg of sodium and then 7 ml of trichloroacetonitrile are added and stirred at the ambient, sheltered from moisture, during 5 h. The reaction is followed by TLC (hexane-ethyl acetate: 9/5). The reaction mixture is filtrated, concentrated and the resulting syrup is chromatographied on silica gel column (150 g of gel) (eluent: hexane-ethyl acetate: 9/5–1.3 g of the more migrating product is obtained (yield: 38.4%).

M.P.=122°–123° C. $[\alpha]_D^{20}=+115.5$ (c=1.6,CHCl$_3$) and 884 mg of the less migrating product (yield: 26.1%).
RMN (CDCl$_3$) of the compound: $\delta$=2.05–2.20 2d (12H) OAc; 4-4.26 m (2H) H$_6$H$_6$'; 4.3–4.6 m (1H) H$_5$;5.4 m (2H) H$_3$H$_4$; 5.55 q (1H) H$_2$; J$_{1,2}$=4 Hz; J$_{2,3}$=2 Hz; 6.60 d (1H) H$_1$; J$_{1,2}$=4 Hz;8.65 s (1H) NH.

(k)—Preparation of 7-methoxycarbonyl 3,6 dioxaheptyl-2-acetamido 6-O-benzoyl 3-O-benzyl-4-O-[2,3,4,6 tetra-O-acetyl-$\beta$-D-galactopyranosyl]2-deoxy-$\beta$-D-glucopyranoside (compound 12) according to the following scheme:

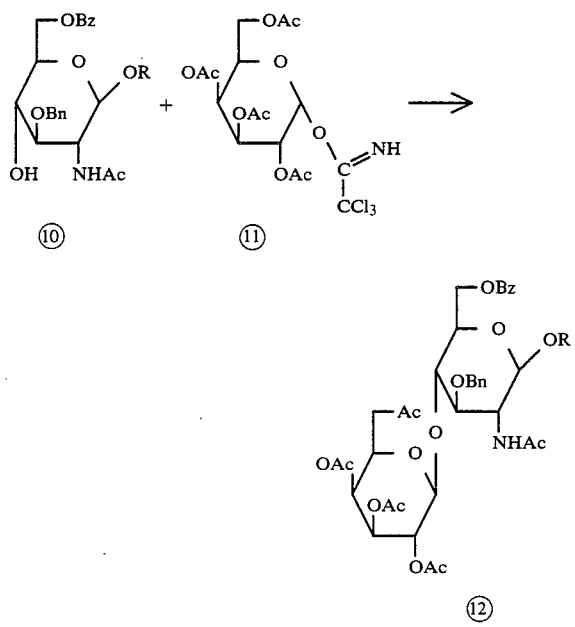

435 mg of aglycon (compound 10) and 600 mg of imidate (compound 11) are dissolved in 2 ml of anhydrous dichloromethane.

8 drops of boron trifluoride etherate are added.

The reaction mixture is stirred, sheltered from moisture, at the ambient during 7 h. To achieve the reaction, 260 mg of imidate are added and after a 14 h stirring, the products are extracted by dichloromethane. The organic phase is washed with sodium bicarbonate and then with water, is dried with sodium sulfate, filtrated and concentrated.

The resulting syrup is chromatographied on a silica-gel column.

[55 g; eluent: CHCl$_3$—acetone 7/3].

475.5 mg of a pure fraction are obtained $[\alpha]_D^{20}=6.9$ (c=1.07; CHCl$_3$).

—starting material 65.2 mg yield with respect to the aglycone which has reacted: 81%.

NMR (CDCl$_3$):=2.00 s–2.12 s–1.16 s (15H) N—Ac. COCH$_3$; 3.50–4.06 m (16H), 4.10 s (2H) O—CH$_2$CO; 4.50–5-50 m (9H); 6.50 d (1H) NH; 7.35–7.70 m (8H) benzyl benzoate m.p.: 8.10 d (2H) benzoate ortho.

(l)—Preparation of 7 methoxycarbonyl 3,6 dioxaheptyl 2 acetamido 6-O benzoyl 4-O [2,3,4,6 tetra-O-acetyl-$\beta$-D-galactopyranosyl]-2-deoxy-$\beta$-D-glucopyranoside (compound 13)

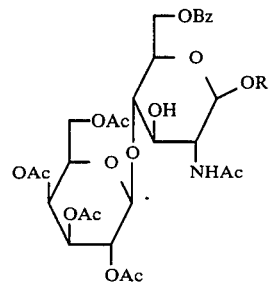

475.5 mg of the starting material are dissolved in 60 ml of anhydrous methanol. About 100 mg of Pd/C 10% are added. The reaction mixture is stirred under hydrogen pressure during 14 h. The reaction is followed by TLC (CHCl$_3$-acetone: 6/4).

After filtration and concentraiton, a syrup is obtained which is chromatographied on a silica gel column (30 g); eluent: CHCl$_3$-acetone: 6/4.

301.5 mg of a colourless syrup are obtained.

Yield 70.3% $[\alpha]_D^{20}=0.43$ (c=4,CHCl$_3$).

NMR spectrum (CDCl$_3$): $\delta$=1.92–2.10–2.20 s (15H) N—Ac CH$_3$CO; 3.50–4.06 m (13H); 4.12–4.30—m (4H); 4.30–5.5 m (8H); 6.70d (1H) NH; 7.30–7.70 (m) 3H; 8.10 d (2H) benzoate ortho.

(m)—Preparation of 1-O-(N-methyl)acetimidyl 2,3,4 tri-O-benzyl-$\beta$-L-fucopyranoside (compound 14) of the formula

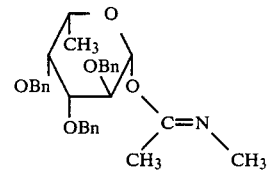

First the Vilsmeier reagent is prepared by mixing PCl$_5$ (1.040 g; 5 mmoles), CCl$_4$ (10 ml), DMF (0.365 ml) and tribenzylfucose (868 mg, 2 mmoles). PCl$_5$ (finely powdered) and percolated CCl$_4$, are poured on Al$_2$O$_3$, under N$_2$ and stirring in a 3 necked flask.

The mixture is stirred 5 mm under nitrogen. DMF distilled on BaO is added by a dropping funnel.

A white precipitate is observed.

The flask is left 10 mn under nitrogen and is plugged. The solution is filtrated in a glove box and the crystals are rinsed with CCl$_4$. The precipitate is added to the tribenzyl-fucose dissolved in 20 ml of dichloromethane.

The mixture is stirred 30 mn sheltered from moisture, (TLC benzene-ether: 13/1).

The solution is extracted by chloroform, washed with water, sodium bicarbonate and then water.

The organic phase is dried with sodium sulfate, filtrated and concentrated. A yellow syrup is obtained. The imidate is prepared as follows:

The following products are stirred under nitrogen, sheltered from light:

N-methylacetamide (162 mg; 2.2 mmoles), molecular sieve 4 Å (powder) and silver oxide (1.16 g) in 20 ml of anhydrous benzene.

The chlorinated derivative is added (syrup) and 0.38 ml of diisopropylethylamine.

After 14 h stirring, the reaction mixture is filtrated on Celite and eluted with 100 ml of ether (containing 0,1% of triethylamine. The solvents are evaporated and a coevaporation with benzene is carried out.

1.17 g of syrup is obtained, recrystalled in hexane. A drop of triethylamine is added. 860 mg of product are obtained.

(yield 88%)—M.P.=88°-89° C. $[\alpha]_D^{20} = -65°$ (c=1.2 benzene).

(n)—Preparation (by reacting compounds 13 and 14), of 7 methoxy-carbonyl 3.6 dioxa heptyl 2 acetamido 6-O benzoyl 3-O [2,3,4 tri-O-benzyl-α-L-fucopyranosyl]4-O [2,3,4,6 tetra-O-acetyl-β-D-galactopyranosyl]2 deoxy-β-D-glucopyranoside (compound 15) of the formula:

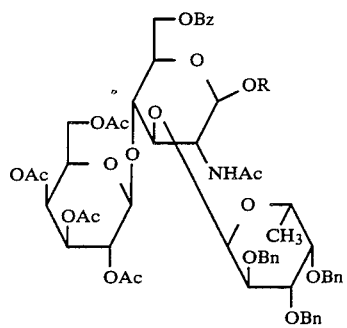

100 mg of aglycone (compound 13) are stirred under argon in 0.6 ml of a solution of paratoluene sulfonic acid (66.9 mg/ml in benzene) and a 4 Å molecular sieve (powder).

After one hour the imidate (compound 14) is added (100 mg). After a stirring of 14 hours, 50 mg of imidate are added.

The reaction is followed by TLC (CHCl₃—acetone: 7/3). The solution is filtered after 8 h on sintered glass and the sieve is rinsed with dichloromethane. Triethylamine is added up to neutral pH and then concentrated. The resulting syrup is chromatographied on a silicagel column.

(12 g) (eluent CHCl₃—acetone: 8/2).

$[\alpha]_D^{20} = -32°$ (c=1,25; CHCl₃).

Condensation yield 85%.

(o)—Preparation of 7 methoxycarbonyl 3,6 dioxaheptyl 2 acetamido 3-O-[2,3,4 tri-O-benzyl-α-L-fucopyranosyl]4-O-[β-D-galactopyranosyl]2 deoxy-β-D-glucopyranoside (compound 16).

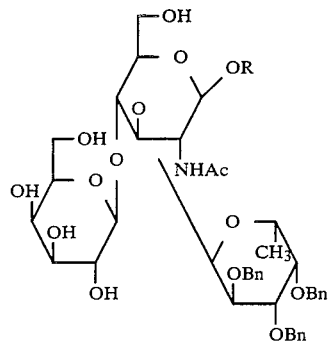

40.6 mg of starting material are dissolved in anhydrous 10 methanol. Some drops of a sodium methylate 2N solution in methanol are added.

The reaction mixture is stirred at the ambient during 30 h.

The reaction is followed by TLC (CHCl₃—MeOH: 6/4-.

After neutralisation with a dry, H⁺, Dowex resin, the solution is filtrated and concentrated. The resulting syrup is chromatographed on a silica gel column (2 g)-eluent CHCl₃-MeOH (6/4).

28.7 mg of a pure fraction are obtained.

Yield: 90%.

$[\alpha]_D^{20} = -76.4°$ (c=1.02: MeOH).

(p)—Preparation of compund 17-

28.7 mg of compound 16 are dissolved in 7 ml of anhydrous methanol.

20 mg of about Pd/C, 10% are added. The mixture is stirred under hydrogen pressure during about 14 h. The reaction is followed by TLC (methanol-ethyl acetate-water=5/4/1). The solution is filtrated on sintered glass and concentrated.

A product (which is homogeneous in TLC). Quantitative yield $[\alpha]_D^{20} = -58.2°$ (c=0.78; methanol).

EXAMPLE 5

Tests relating to specific recognition of the 3-fucosyllactosamine sequence

The results of tests (a) and (b) are reported below.

In the tests (a), the inhibition of the fixation of anti-SSEA-1 to meconium of human origin marked with $I^{125}$, is studied by on the one hand, various natural oligosaccharides (that is to say constituting chains of natural products), on the other hand, 3-fucosyl-lactosamine itself, obtained by synthesis and a synthetic tetrasaccharide.

The tests (b) relate to the study of the inhibition of the fixation of anti-SSEA-1 to meconium marked by $I^{125}$ by meconium, placenta, and amniotic fluid, all three of human origin.

These tests were carried out according to radioimmunological techniques with the use of two antibodies. The determination method used corresponds to a method modified with respect to that described by Wood, E., Lecomte J., Childs, R. A. & FEIZI, T. Mol. Immunol. 16, 813–819 (1979)

The anti-SSEA-1 antibodies (dilution 1:3000 in phosphate buffer, bovine albumin serum) is obtained from a BALB/c mouse ascites liquid treated with prispane, and to which has been injected hybrid cells producing antibodies.

As a vehicle, normal mouse serum (dilution 1:100) was used.

The second antibody was constituted by a rabbit immunoglobin antimouse serum, undiluted (of Dakoimmunoglubulins, Copenhagen, Denmark).

Tests a—The oligosaccharides used are the following (for each of them is indicated the symbol used on the curves given in FIG. 1, their structure and their designation).

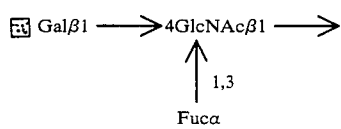

6?- 3 hexenetetrol(s) N—1 R_L 0.71a

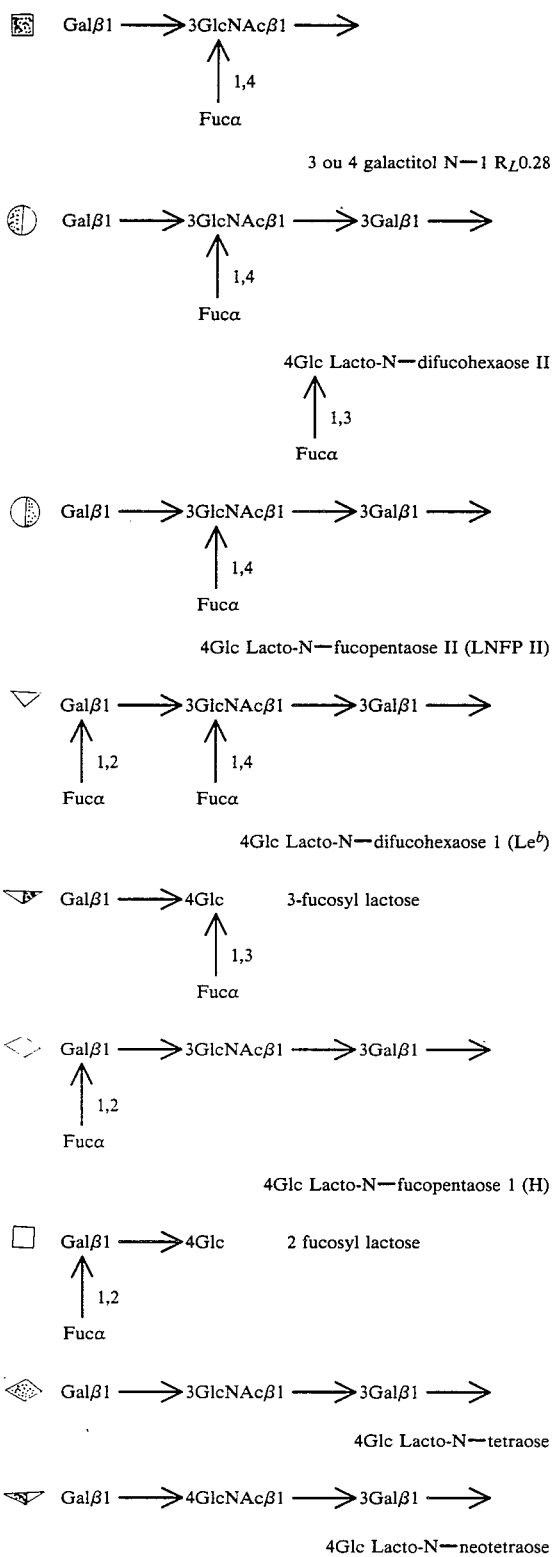

-continued

⊠ Galβ1 ⟶ 3GlcNAcβ1 ⟶
            ↑ 1,4
            Fucα

3 ou 4 galactitol N—1 R_L 0.28

Galβ1 ⟶ 3GlcNAcβ1 ⟶ 3Galβ1 ⟶
            ↑ 1,4
            Fucα

4Glc Lacto-N—difucohexaose II
            ↑ 1,3
            Fucα

Galβ1 ⟶ 3GlcNAcβ1 ⟶ 3Galβ1 ⟶
            ↑ 1,4
            Fucα

4Glc Lacto-N—fucopentaose II (LNFP II)

▽ Galβ1 ⟶ 3GlcNAcβ1 ⟶ 3Galβ1 ⟶
       ↑ 1,2        ↑ 1,4
       Fucα         Fucα

4Glc Lacto-N—difucohexaose 1 (Le^b)

Galβ1 ⟶ 4Glc    3-fucosyl lactose
            ↑ 1,3
            Fucα

Galβ1 ⟶ 3GlcNAcβ1 ⟶ 3Galβ1 ⟶
       ↑ 1,2
       Fucα

4Glc Lacto-N—fucopentaose 1 (H)

☐ Galβ1 ⟶ 4Glc   2 fucosyl lactose
       ↑ 1,2
       Fucα

Galβ1 ⟶ 3GlcNAcβ1 ⟶ 3Galβ1 ⟶

4Glc Lacto-N—tetraose

Galβ1 ⟶ 4GlcNAcβ1 ⟶ 3Galβ1 ⟶

4Glc Lacto-N—neotetraose

They are oligosaccharides with (Gal β1→3GlcNac), sequences, called type 1 or (Gal β1→4GlcNac/Glc) called type 2.

The results of these inhibition tests are reported in FIG. 1.

It appears that the oligosaccharides with sequences of type 1 are inactive as inhibitors of anti-SSEA-1.

On the other hand, very considerable inhibition appears with the oligosaccharide called N-1 R_L 0.71a which contains a fucosylated sequence of type 2.

In fact, 0.5 nmole gives an inhibition of 50%.

This oligosaccharide was isolated from an N-1 glycoprotein, after partial alkaline degradation (Lloyd, K. O., Kabat, E. A. & Licerio, E. Biochemistry, 7, 2976-2990 (1968).

It is interesting to note the weak inhibition obtained with the oligosaccharide including the 3-fucosyl-lactose sequence, which indicates the importance of the N-acetyl-glucosamine group in the function of SSEA-1 as an antigen determinant.

The active oligosaccharides Le^a(Lewis^a) possessing a structure of type 1 with a terminal sequence

Galβ1 ⟶ 3GlcNAc
            ↑ 1,4
            Fucα are revealed to be at least 10 times less active than their isomers of type 2. Further, it has been shown that this activity was due to the presence of isomers of type 2, (it will be noted that it concerns, in fact, products of natural origin which are hence not pure). Lacto-N-difucohexose I (active Le^b), lacto-N-fucopentose I (active H) and 3-fucosyl-lactose appear 200 to 1000 times less active as inhibitors.

2-fucosyl-lactose, lacto-N-tetraose and lacto-N-neotetraose show themselves to be inactive.

All of these results show well the specific recognition by the anti-SSEA-1 of the 3-fucosyl-N-acetylic lactosamine structure as an antigenic determinant.

Confirmation of these results is given by studying the inhibition obtained with 3-fucosyl-lactosamine prepared according to the method of JACQUINET and SINAY mentioned above and the tetrasaccharide O-α-L-Fucopyranosyl-(1→2)-O-β-D-galactopyranosyl-(1→4)-O-[α-L-fucopyranosyl-(1→3)]-2-acetamido-2-deoxy-D-glucopyranose Galβ1 ⟶ 4GlcNAc
       ↑ α 1,2   ↑ α 1,3
       Fuc        Fuc prepared according to JACQUINET and SINAY, J.O.C. 42,720, 1977.

Figure 2:
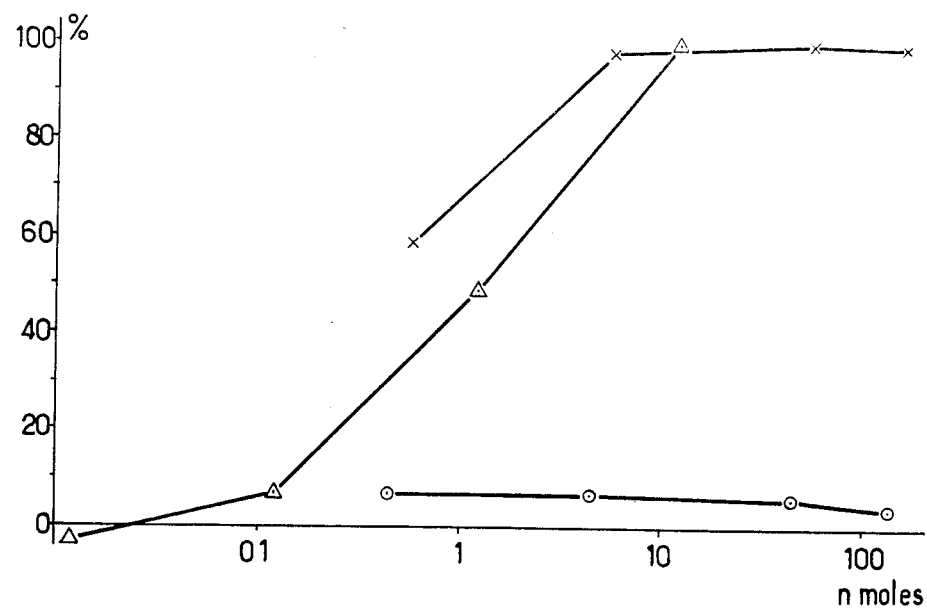

The results of the inhibition observed are reported in FIG. 2 (curve with X) whose examination shows complete inhibition of the fixation, whereas no effect is observed with the synthetic tetrasaccharide.

These results establish clearly the recognition as an antigen of the trisaccharide sequence concerned.

Tests b—By proceeding as previously, there were used as inhibiting substances placenta, meconium and amniotic fluid of human origin.

Figure 3:
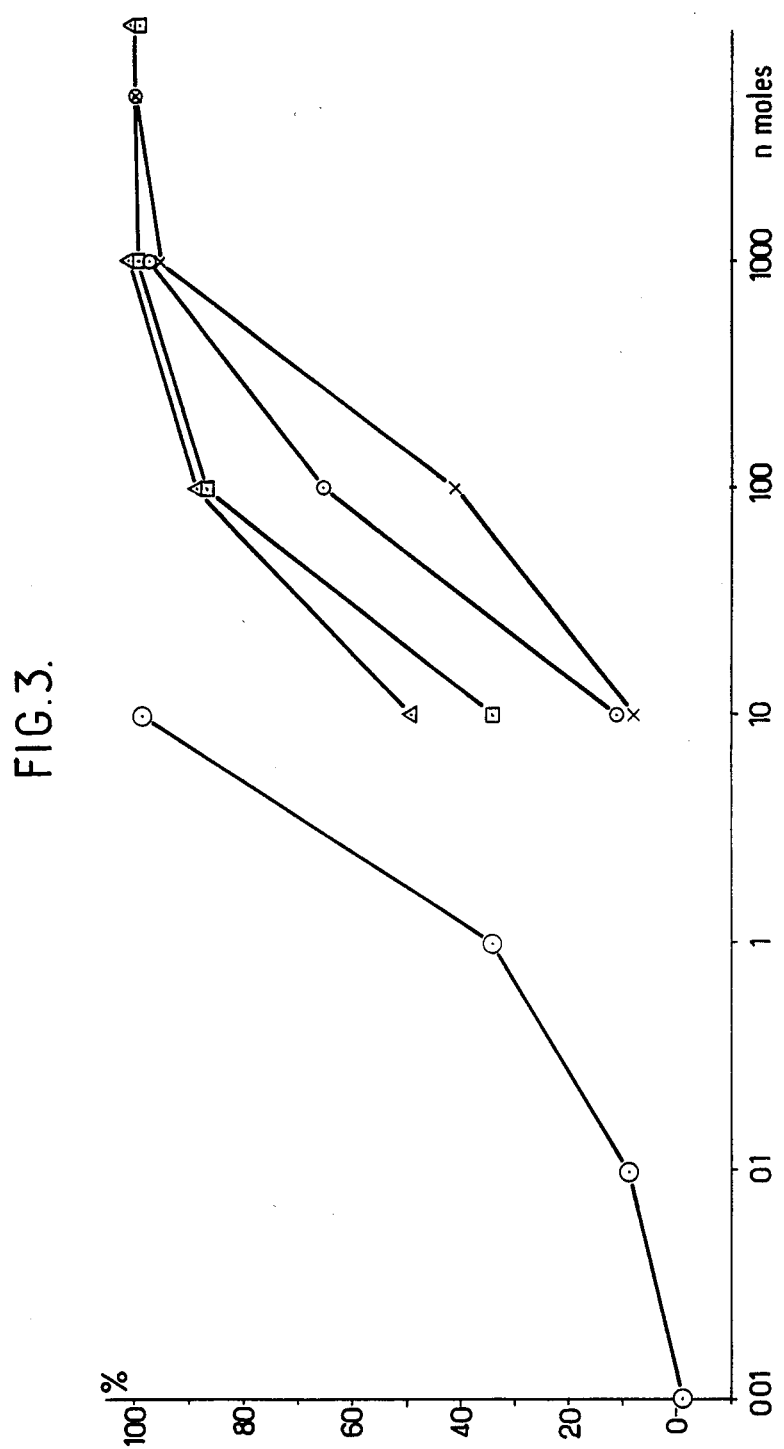

The inhibition results obtained are reported in FIG. 3 where the symbol ⊗ relates to meconium X and ⊙ to two tests on placenta, △ and ▣ to two tests on amniotic fluid.

It emerges from these results that the 3-fucosyl lactosamine sequence is expressed in the substances studied where it can hence be advantageously demonstrated with the reagents of the invention for diagnostic purposes of developments in pregnancies.

EXEMPLE 6

Preparation of an artificial antigen by means of the trisaccharide of Example 2 and use as a diagnostic reagent According to methods known in themselves, (activation, then fixation), there were fixed, in different tests, the trisaccharide of Example 2, having a substituent chain with an amino termination, respectively on beads of latex, of glass and of agarose.

The conjugated antigen, so prepared was contacted with the serum to be tested. In this manner an agglutination reaction was produced, which enabled the detection of the presence of antibodies in the serum.

This test is particularly interesting to recognize the presence of anti-3-fucosyl N-acetyl lactosamine antibodies in the serum of a pregnant woman.

EXAMPLE 7

Development of specific antibodies by means of the trisaccharide of Example 3 and application to the detection of teratomas.

Known techniques for the fixation of the trisaccharide of Example 3 were followed on different carrier vehicles, namely, albumin, bovinserum albumin, thyroglobulin, poly-L-alanine-Lysine and polylysine which are supports compatible with administration to the animal.

The antigen thus fixed was administered to the rabbit and an immunserum was collected which was purified to obtain the specific immunoglobulins.

This specific antibody was fixed on latex beads (in other tests glass beads or agarose beads were used) and permitted the identification by the agglutination reaction of the 3-fucosyl-N-acetyl lactosmine antigen in a teratoma.

EXAMPLE 8

By using the derivative according to example 4, fixed on poly-lysine and by raising specific antibodies, a gastro intestinal tumor was detected.

In that respect, it will be noted that the 3-fucosyl-N-acetyl lactosamine sequence is the antigenic determinant of various kinds of tumors—which are then detectable with the means provided by the invention.

These antibodies raised as above described and labelled with a tracer, specific or not, compatible with administration in human being ($I^{131}$, $Tc^{99}$ for example) can thus be used for in vivo detections and localizations of tumors.

These antibodies can also be used in medicine for anti-tumor therapy. They can be prepared as a pharmaceutical preparation particularly of injectable use.

They can be used either as such for intra- or peritumoral administration or encapsulated in liposomes or also as homing substances associated or conjugated to anti-tumor substances or in other appropriate way well known by the man of the art.

We claim:

1. Trisaccharides of the formula:

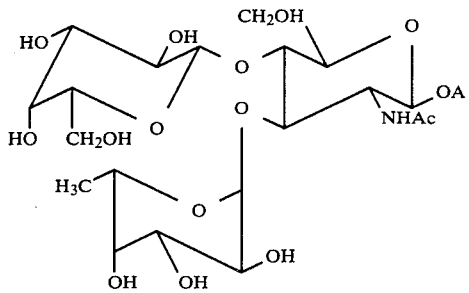

wherein
A is a hydroxy-alkyl group of 2 to 10 carbon atoms, an alkenyl group of 2 to 10 carbon atoms or one of the following substituents:

(1):— $(CH_2)_n$—O—$(CH_2)_{n'}$—O—$(CH_2)_m$—R (2):— $(CH_2)_{n''}$—O—$(CH_2)_{m'}$—R (3):— $(CH_2)_{n'''}$—R wherein
—n,n' and m, are identical or different each from other and are equal to 1,2,3,4 or 5, with m being further equal to 0, —n" and m' are identical or different each from other, being equal to 1,2,3,4 or 5 with m' being further equal to 0, n"+m' (where m' is not 0) being an integer from 4 to 10,
—n''' is an integer from 1 to 10 and —R is hydrogen, where m=0 in (1), OH, and COOR' wherein R' is alkyl or alkenyl of 2-10 carbon atoms, —COOH, —CONH$_2$ N$_3$ or —NH$_2$
and
B is hydrogen.

2. Trisaccharides according to claim 1 wherein, the sum n+n'+m is an integer equal to 8.

3. Trisaccharides according to claim 1, comprising an A substituent of structure (1) or (2) wherein R is a hydrogen atom.

4. Trisaccharides according to claim 1, wherein A is a chain having structure (1), (2) or (3), R is a —COOR', where R' is an alkyl group with 2 or 3 carbon atoms, or R is a —CONH$_2$ group.

5. Trisaccharides according to claim 1 wherein R is a nitrogenous group selected from the group consisting of —NH$_2$, —N$_3$ or —NH—NH$_2$.

6. Trisaccharides according to claim 1 wherein A is the substituent (1) or (2) wherein —R is an alkenyl group of 2 to 10 carbon atoms.

7. Trisaccharides according to claim 1 wherein n"+m' is equal to 8 provided m' is other than 0.

8. Trisaccharides according to claim 1 wherein n''' is an integer from 4 to 10.

9. Trisaccharides according to claim 1 wherein A has the structure (1) or (2) and R is an allyl group.

10. Trisaccharides according to claim 1 selected from the group consisting of
8-azido-3,6-dioxaoctyl 2-acetamido-3-O [α-L-fucopyranosyl]-4-O [β-D-galactropyranosyl]-2-deoxy-β-D-glycopyranoside;
8-amino 3,6-dioxaoctyl 2 acetamido-3-O [α-L-fucopyranosyl]-4-O-[β-galactopyranosyl]-2-deoxy-β-D-glucopyranoside;

8-methoxy carbonyl octyl 3,6-dioxa 2-acetamido 3-O-[αL-fucopyranosyl]-4-O[β-D-galactopyranosyl]2-deoxy-β-D-glucopyranoside.

11. An immunological reagent which comprises a reactively effective and detectable amount of trisaccharide according to claim 1 in admixture with a suitable carrier.

12. A diagnostic reagent which comprises a reactively effective and detectable amount of trisaccharide according to claim 1 in admixture with a suitable carrier.

13. An artificial antigen composition which comprises a reactively effective and detectable amount of trisaccharide according to claim 1 fixed to a suitable water soluble macromolecular support.

14. An immunoabsorbant composition which comprises a reactively effective and detectable amount of trisaccharide according to claim 1 fixed to a suitable insoluble macromolecular support.

15. Antibodies specific with respect to a trisaccharide according to claim 1 formed by a predetermined immunologically active system in response to contact with a trisaccharide according to claim 1 or 3-fucosyl-N-acetyl lactosamine.

16. A method of detecting anti-3-fucosyl-N-acetyl lactosamine antibodies in serum which comprises contacting the serum to be tested with the artificial antigen composition according to claim 13 or 3-fucosyl-N-acetyl lactosamine and observing the presence or absence of antibody/antigen reaction.

17. A method of detecting the localizing in vivo gastro intestinal tumors which comprises administering to the host respected of having such tumors, antibodies according to claim 15 labeled with a physiologically acceptable radioactive tracer and observing the location of areas of elevated radioactivity in said subject.

18. An immunoabsorbant composition which comprises a reactively effective and detectable amount of trisaccharide according to claim 1 fixed to a suitable water insoluble macromolecular support selected from the group consisting of cellulose, agarose or recticulated agarose, silica, glass, latex beads and copolymers of polyacrylamide.

19. An artificial antigen composition which comprises a reactively effective and detectable amount of trisaccharide according to claim 1 fixed to a suitable water soluble macromolecular support wherein the said support is a protein.

20. A composition according to claim 19, wherein the protein is selected from poly-L-alanine, -lysine, albumin, bovin serum albumin, thyroglublin and polylysine.

* * * * *